(12) United States Patent
Muir et al.

(10) Patent No.: US 6,752,757 B2
(45) Date of Patent: Jun. 22, 2004

(54) OXIDATION-RESISTANT COATINGS

(75) Inventors: Andrew Muir, Surrey (GB); Walid Abi Aoun, Oxfordshire (GB); Steven Short, Wiltshire (GB)

(73) Assignee: Sterilox Technologies International Limited, Oxfordshire (GB)

( * ) Notice: Subject to any disclaimer, the term of this patent is extended or adjusted under 35 U.S.C. 154(b) by 4 days.

(21) Appl. No.: 10/133,914

(22) Filed: Apr. 26, 2002

(65) Prior Publication Data

US 2002/0165431 A1 Nov. 7, 2002

(30) Foreign Application Priority Data

Apr. 27, 2001 (GB) ............................................. 0110390

(51) Int. Cl.$^7$ ................................................. A61B 1/00
(52) U.S. Cl. ........................................ 600/133; 422/20
(58) Field of Search .............................. 600/101, 133; 422/20

(56) References Cited

U.S. PATENT DOCUMENTS

| | | | | |
|---|---|---|---|---|
| 3,657,760 A | * | 4/1972 | Kudisch | .................. 15/104.93 |
| 4,064,061 A | * | 12/1977 | Henry | ..................... 15/104.93 |
| 4,877,781 A | * | 10/1989 | LaHaye et al. | ............. 514/179 |
| 4,896,768 A | * | 1/1990 | Anderson | .................... 206/210 |
| 4,981,756 A | | 1/1991 | Rhandhawa | |
| 4,998,984 A | * | 3/1991 | McClendon | ................. 206/205 |
| 5,120,596 A | | 6/1992 | Yamada | |
| 5,562,642 A | * | 10/1996 | Smith et al. | ................. 604/289 |
| 5,693,050 A | | 12/1997 | Speiser | |
| 5,716,322 A | * | 2/1998 | Hui et al. | .................... 600/133 |
| 5,802,440 A | * | 9/1998 | Maeyama | ..................... 430/99 |

FOREIGN PATENT DOCUMENTS

| | | |
|---|---|---|
| EP | 0 605 243 A1 | 7/1994 |
| EP | 1 059 333 A1 | 12/2000 |
| EP | 1 066 839 A1 | 1/2001 |
| GB | 1036938 | 7/1966 |
| GB | 2 353 954 A | 3/2001 |
| JP | 61-08295 A | 1/1986 |
| WO | 92/11061 A1 | 7/1992 |

\* cited by examiner

*Primary Examiner*—John P. Leubecker
*Assistant Examiner*—H M. Johnson
(74) *Attorney, Agent, or Firm*—Akin Gump Strauss Hauer & Feld, L.L.P.

(57) ABSTRACT

A method is provided for protecting a medical instrument and other articles adapted to be inserted into and removed for re-use from a human or animal body. A temporary coating of an oxidation-resistant material is applied to the instrument or part thereof to protect the instrument or part thereof over at least one sterilizing or disinfecting cycle. A suitable applicator for the coating includes a support medium loaded with the oxidation-resistant material

19 Claims, No Drawings

OXIDATION-RESISTANT COATINGS

BACKGROUND OF THE INVENTION

The present invention relates to sterilization- or disinfection-resistant coatings for endoscopes and similar medical apparatus which require sterilization or disinfection between uses.

Endoscopes and other reusable medical devices designed for insertion into the human or animal body generally require sterilization or disinfection between uses. Traditionally, sterilization or disinfection of medical equipment is achieved by autoclaving, i.e., by exposing the equipment to steam at high temperature and pressure. While this method is effective, it is often unsuitable for complex and relatively delicate apparatus, such as endoscopes, which may include components that are not heat-resistant. In order to solve this problem, it has been proposed to use organic sterilizing solutions such as glutaraldehyde at ambient temperatures. However, glutaraldehyde has limited sterilizing activity, especially in relation to bacterial spores, and can also cause allergic reactions in staff.

A recent improvement has been the use of sterilizing solutions, which are oxidizing in nature, such as peracetic acid and chlorine dioxide, among others. A number of recently-developed oxidizing, sterilizing or disinfecting solutions may be produced, for example by way of electrochemical processing of aqueous salt solutions, as disclosed for example in GB 2316090A. These solutions, such as sold under the Sterilox™ trademark, are produced by electrochemical cells comprising an anode chamber and a cathode chamber separated by a permeable membrane, and include oxidized chlorine species, such as hypochlorous acid, as sterilizing agents. Such solutions are highly effective in their sterilizing action, but are more aggressive than, for example, glutaraldehyde and can attack the plastics and similar components which are used in the construction of endoscopes and the like. The mechanism of degradation is unknown but may involve hydrolysis and/or oxidation.

Traditional chemicals used for disinfection require specialist handling, extensive fume extraction, and the spent material requires specialist disposal. They also have typical sterilization cycles of up to one hour. In contrast, the oxidizing sterilizing solutions, such as Sterilox™ solution, have a much shorter recommended contact time, are non-toxic, non-sensitizing, do not need extraction and can be disposed of safely into mains drainage. In other words, these solutions show advantages in terms of potency, speed of use, safety of use and environmental impact over traditional chemicals used to sterilize endoscopes.

However, it has been found that, under certain conditions of sterilization or disinfection using these oxidizing solutions, the lacquer covering of some flexible endoscopes can suffer surface degradation, especially of the patient insertion tube and/or light guide. The polymer surface absorbs water and becomes tacky, which can result in poorer, handling characteristics for medical staff.

UK Patent Application No. GB 2353954A describes a coating process developed by the Applicant to protect medical instruments such as endoscopes. The process involves coating a polycarbonate-based polyurethane material, in particular by spraying, onto the lacquer to minimize and substantially reduce the degradation of the lacquer when instruments are disinfected using oxidizing solutions.

Despite the success of the coating, there are still some problems associated with the coating method. For example, the coating may only be applied by trained operatives in specially constructed clean environments with extraction and curing facilities. This means that hospitals tend to send their endoscopes away for at least 72 hours to be coated and, consequently, this has adverse effects on the management of operations within a hospital ward. For those countries where the coating process is not available, the endoscopes must be sent abroad, thereby significantly increasing the period for which the hospital must cope without the endoscope.

Although the chemical coatings described in GB 2353954A have shown good compatibility with sterilizing solutions, such as Sterilox™ solution, both in the actual use and in accelerated tests, endoscopes tend to be handled and cleaned differently in each hospital. In some cases, the detergents used can be very Aggressive to these coatings and the handling and cleaning procedures may, in some instances, damage the coating.

In view of the above, Applicant has sought to develop a method and a coating to substantially eliminate the degradation of lacquer on medical instruments, such as endoscopes and overcome the problems associated with the method described in GB 2353954A.

BRIEF SUMMARY OF THE INVENTION

Accordingly, in one aspect of the present invention there is provided a method of protecting a medical instrument or part thereof, adapted to be inserted into and removed for re-use from a human or animal body, against an oxidizing sterilizing or disinfecting solution by applying a coating of an oxidation-resistant material, characterized in that the instrument or part thereof is coated with a temporary coating which protects the instrument or part thereof over at least one sterilizing or disinfecting cycle.

The temporary coating must be sufficiently durable to withstand at least one sterilizing or disinfecting cycle. If applied prior to manual cleaning of the instrument, the coating should be resistant to the process of brushing with detergent. In order to be certain that the instrument or part thereof is adequately protected against the oxidizing solution, a fresh coating of the oxidation-resistant material is preferably applied before every sterilizing or disinfecting cycle. In this way, personnel responsible for maintaining and preparing the medical instruments for use are not required to keep and consult records of the number of sterilizing cycles an instrument has been subjected to before deciding whether to apply a further coating. In practice, however, an instrument or part thereof may only require coating after, say, every five to ten sterilizing or disinfecting cycles in order to maintain the desired protective shield. The frequency of application will depend on the material of construction of the instrument, the detergents used, the type of disinfectant and the duration of the disinfection cycle.

The application of a temporary coating should be such that the coating may be applied without the need for complicated, numerous or lengthy procedures. Ideally, the oxidation-resistant material may be applied to the instrument or part thereof by wiping, but may also be applied by any appropriate method such as brushing, dipping or spraying.

Such a method of application is quick, requires no expertise and may be carried out by a user, such as a nurse, within the environs of a hospital. Furthermore, the instrument may be ready for sterilization within minutes of being coated thereby minimising the time that an instrument cannot be used.

Preferably, the method involves wiping the instrument or part thereof with a support medium, such as a cloth or pad, loaded with the oxidation-resistant material. It is advantageous if the support medium is saturated with the material to ensure that sufficient material is applied.

To minimize the introduction of bacteria, microbes and the like, it is further preferred if the support medium and oxidation resistant materials are sterile.

From another aspect, the invention also encompasses an applicator for applying a temporary coating of an oxidation-resistant material to a medical instrument or part thereof, the instrument or part thereof being adapted to be inserted into and removed for re-use from a human or animal body, wherein the applicator comprises a support medium loaded with the oxidation-resistant material.

Advantageously, the applicator is packaged in a sealed wrapping, thereby preventing the premature evaporation of any diluent and maintaining the sterility of the applicator.

The Applicant has found that polytetrafluoroethylene (PTFE) is particularly suited to this application. However, it will be appreciated that other suitable compounds, compositions and materials may be used. Advantages of using PTFE are that its application is relatively non-toxic and non-hazardous, the procedure may take place in a hospital and takes less than five minutes per article.

While the oxidation-resistant material may be applied in the form of a wax or oil, for example, the material may be also applied in a diluent, for example as an emulsion or dispersion. It is advantageous if the diluent is capable of evaporating to leave a substantially dry coating within about 10 minutes from application. In this way, the time needed to coat and re-coat an instrument is minimized. A further advantage is seen if diluent has a boiling point no greater than the boiling point of water so that the coating may be air-dried or dried by the application of a short burst of heat.

In particular, the Applicant has found that PTFE may be applied as a suspension in an appropriate diluent such as isopropanol or water. An example of a suitable suspension is commercially available under the trademark Microcoat and supplied in the UK by Holscot Industrial Linings.

The method may also include polishing the coated instrument to remove excess oxidation-resistant material and to ensure even and complete coverage of the coating after the material has been applied and, if the material is applied in a diluent, after drying.

The application of a temporary protective coating to endoscopes and the like which are disinfected in oxidizing solutions, such as Sterilox™ solution, substantially reduces or eliminates damage to the surface of the flexible endoscope tubes, does not change the clinical performance of the endoscope and does not increase the risk to the patient as a consequence of the clinical procedure.

From a further aspect, the invention encompasses the use of polytetrafluoroethylene as a temporary oxidation-resistant coating on a medical instrument or part thereof adapted to be inserted into and removed for re-use from a human or animal body.

According to a yet further aspect of the present invention, there is provided a medical instrument or part thereof adapted to be inserted into and removed for re-use from a human or animal body, characterized in that the instrument or part thereof has a temporary coating of polytetrafluoroethylene.

BRIEF DESCRIPTION OF THE SEVERAL VIEWS OF THE DRAWINGS

FIG. 1 is a schematic representation of an endoscope as an example of a medical instrument to be coated according to the present invention; and FIG. 2 is a schematic representation of an applicator, such as an impregnated cloth, in a sealed wrapping according to the present invention.

DETAILED DESCRIPTION OF THE INVENTION

The present invention will now be illustrated by way of the following example.

New and clinically used endoscope insertion tubes and a new light guide were used to test the efficacy of the application of a suspension of PTFE as a wipe. The tubes and light guide were divided into sections referred to as Sections A, B, C, D and E respectively.

Sections A were used as controls and were not treated by the PTFE wipe. Sections B were treated by the PTFE wipe after each cycle. Sections C were treated by the PTFE wipe after every five cycles. Sections D were treated by the PTFE wipe after every ten cycles. Sections E were treated by the PTFE wipe every thirty cycles.

The sterilizing or disinfecting cycle referred to above involves the following steps:

Hand wash using warm water and detergent.

Running the insertion tubes and the light guides in a washer disinfector for a wash with detergent, followed by a water rinse, followed by disinfection with Sterilox™ oxidizing solution and finally rinsed with diluted Sterilox™ oxidizing solution.

The results showed that Sections A show degradation of the lacquer after 76 cycles. Sections B and C show no degradation of the lacquer even after 265 cycles. Sections D and Sections E show partial degradation of the lacquer after 160 to 190 cycles.

It should be noted that the present invention is directed specifically towards endoscopes and other re-usable medical instruments, which are intended to be inserted temporarily, e.g. for up to 24 hours, into the human or animal body and then removed, as opposed to devices such as replacement heart valves and the like which are designed for permanent or long-term implantation. Because endoscopes and the like are used more than once and will generally be used on different patients, it is vital that they be sterilized between uses. It will be appreciated that the coating need not be applied to the whole article in question but merely to the or each part which is to be inserted into the body and therefore requires sterilization or disinfection before and cleaning after each use, or only to the part(s) which are known to suffer damage as a consequence of exposure to oxidizing disinfectants.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of protecting a medical instrument or part thereof adapted to be inserted into and removed for re-use from a human or animal body against an oxidizing sterilizing or disinfecting solution, comprising applying a coating of an oxidation-resistant material, wherein the instrument or part thereof is coated with a temporary coating which protects the instrument or part thereof over at least one sterilizing or disinfecting cycle, wherein the oxidation-resistant material is applied from a support medium loaded with the material.

2. The method according to claim 1, wherein the coating of oxidation-resistant material is applied to the instrument or a part thereof by wiping.

3. The method according to claim 1, wherein the support medium is saturated with the oxidation-resistant material.

4. The method according to claim 1, wherein the support medium is sterile.

5. The method according to claim 1, wherein the support medium is a cloth or pad.

6. The method according to claim 1, wherein the oxidation-resistant material is polytetrafluoroethylene.

7. The method according to claim 6, wherein the medical instrument is an endoscope.

8. The method according to claim 1, wherein the oxidation-resistant material is applied in a diluent which is capable of evaporating to leave a substantially dry coating within about 10 minutes from application.

9. The method according to claim 8, wherein the diluent has a boiling point no greater than the boiling point of water.

10. The method according to claim 9, wherein the diluent is water.

11. The method according to claim 9, wherein the diluent is isopropanol.

12. The method according to claim 1, wherein after application of the oxidation-resistant material, and after drying, if the material is applied in a diluent, the coated instrument or part thereof is polished to remove excess material.

13. An applicator for applying a temporary coating of an oxidation-resistant material to a medical instrument or part thereof, the instrument or part thereof being adapted to be inserted into and removed for re-use from a human or animal body, the applicator comprising a support medium loaded with the oxidation-resistant material, the support medium being adapted to apply the temporary coating by wiping, wherein: the support medium is a cloth or pad; the oxidation-resistant material is polytetrafluoroethylene; and the oxidation-resistant material is loaded in a diluent which is capable of evaporating to leave a substantially dry coating within about 10 minutes from application.

14. The applicator according to claim 13, wherein the applicator is packaged in a sealed wrapping.

15. The applicator according to claim 13, wherein the support medium is saturated with the oxidation-resistant material.

16. The applicator according to claim 13, wherein the support medium is sterile.

17. The applicator according to claim 13, wherein the diluent has a boiling point no greater than the boiling point of water.

18. The applicator according to claim 17, wherein the diluent is water.

19. The applicator according to claim 17, wherein the diluent is isopropanol.

* * * * *